Figure 1:
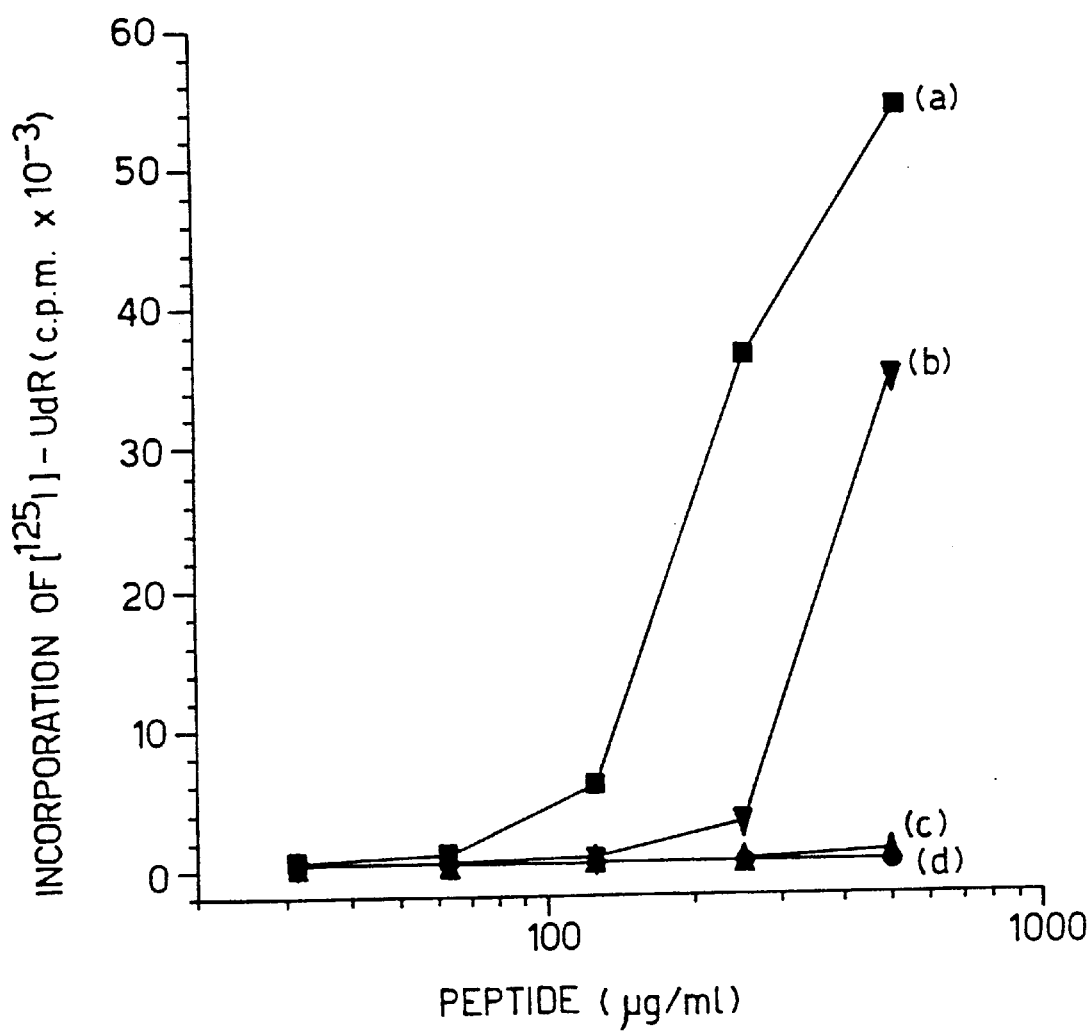

United States Patent [19]
Anderson et al.

[11] Patent Number: 5,969,099
[45] Date of Patent: Oct. 19, 1999

[54] GROWTH FACTOR ANALOGS

[75] Inventors: Derek W. Anderson, Salisbury; John M. Mellor, Southampton; Nigel G. J. Richards, Southampton; Karen J. Sargood, Southampton; David L. Turner, Southampton; Ram P. Sharma, Southampton; Donna E. Davies, Southampton; Stephen G. Chamberlin, Southampton; Audrey Richter, Southampton, all of United Kingdom

[73] Assignee: The Secretary of State for Defence, United Kingdom

[21] Appl. No.: 08/861,000

[22] PCT Filed: Jan. 12, 1996

[86] PCT No.: PCT/GB96/00052

§ 371 Date: Dec. 11, 1997

§ 102(e) Date: Dec. 11, 1997

[87] PCT Pub. No.: WO96/21676

PCT Pub. Date: Jul. 18, 1996

[30] Foreign Application Priority Data

Jan. 13, 1995 [GB] United Kingdom .................. 9500660

[51] Int. Cl.⁶ ..................................................... C07K 7/00
[52] U.S. Cl. .............................. 530/327; 530/399; 514/14
[58] Field of Search .................................... 530/327, 399; 514/14

[56] References Cited

U.S. PATENT DOCUMENTS 4,686,283  8/1987  Nestor et al. ........................... 530/327

FOREIGN PATENT DOCUMENTS

WO A 91
01141      2/1991  WIPO .
9621676 A1 7/1996  WIPO .

OTHER PUBLICATIONS

Acta Chem. Scand. (1992), 46(3), 266–70 Coden: ACHSE7;ISSN: 0904–213X, 1992, XP002002947 Bahr, Josephine et al: Antigenic properties of the second loop of transforming growth factor.alpha. by synthetic peptides.

International Journal of Peptide and Protein Research, vol. 39, No. 5, May(1992,) Copenhagen DK, pp. 464–471, XP002002948 J.P. Tam and X.–Y. Shen: "Efficient approach to synthesis of two–chain asymmetric cysteine analogs of receptor–binding region of transforming growth factor–alpha".

J. Biol. Chem. (1995), 270(36), 21062–7 Coden: JBCHA3:ISSN: 0021–9258, Sep. 8, 1995, XP002002949 Chamberlin, Stephen G. et al: "Constrained peptide analogs of transforming growth factor–.aplha.residues cysteine 21–32 are mitogenically active. Use of proline mimetics to enhance biological potency".

*Primary Examiner*—Cecilia J. Tsang
*Assistant Examiner*—C. Delacroix-Muirheid
*Attorney, Agent, or Firm*—Nixon & Vanderhye

[57] ABSTRACT

A peptide having growth factor type activity (mitogenic and agonist/antagonist for the EGF receptor) which is a TGF-α analog but contains a bicyclic Pro analog (for instance D-2-azabicyclo[2,2,1]heptane-3-carboxylic acid), an N-terminal Phe or Trp residue, and a disulfide bridge.

16 Claims, 3 Drawing Sheets

GROWTH FACTOR ANALOGS

The present invention relates to peptides having growth factor receptor activity, and in particular to peptides which are analogs of Transforming Growth Factor-Alpha (TGFA). The invention further relates to uses of such peptides.

Growth factors represent a group of polypeptides which induce inter alia cell division. TGFA and the closely related Epidermal Growth Factor (EGF) have a role in a number of normal physiological processes such as wound healing.

The sequence and three dimensional structure of both EGF and TGFA have been determined (Campbell et al, Prog. Growth Factor Res. 1989, 1, 13–22). EGF is a 53 amino acid polypeptide (Sequence I.D. No. 1). TGFA is a 50 amino acid polypeptide (Sequence I.D. No. 2) having about 40% homology of residues with EGF. Both peptides are characterised by three well defined loops (denoted A, B and C) and have three intramolecular disulphide bonds.

Several growth factors, including TGFA and EGF, are believed to exert their biological effects via interaction with the Epidermal Growth Factor Receptor (EGF Receptor). The EGF Receptor is a Type 1 receptor tyrosine kinase. The EGF Receptor and its ligands are of interest for their roles in normal physiological processes as well as in hyperproliferative and neoplastic diseases.

A number of studies have been made to establish structure-function relationships within EGF and TGFA so as to be able to design suitable investigative or therapeutic agents (such as EGF Receptor agonists and antagonists). These studies have been made on the well established basis that the sequence of amino acids from which a polypeptide or protein is composed (or primary structure) has a profound effect on its three dimensional (secondary, tertiary and quarternary) structure. The three dimensional structure will in turn affect the function and activity of the polypeptide or protein.

Thus by altering (either randomly or rationally) the number or sequence of amino acids in a peptide, properties such as its kinetics, stability, protease or thermal resistance, specificity and ligand-receptor interactions may be controlled.

Thus in EGF it has been reported that synthetic fragments corresponding to the B-loop bind to the EGF Receptor and have weak mitogenic activity (Komoriyam et al, Proc. Natl. Acad. Sci. USA 1984, 81, 1351). Analogs of the C-loop also have biological activity (Bailie, J. R. et al, Int J, Peptide Protein Res. 1994, 43, 225). Residue 47 (leucine) near the C-terminus of the peptide has also been shown to be important in binding and mitogenesis (Ray, P. et al, Biochemistry 1988, 27, 7289).

In TGFA it has been reported that synthetic peptides corresponding to the B-loop bind only weakly to the EGF Receptor and do not invoke a mitogenic response (see, eg Defeo-Jones, D. et al Mol. Cell. Biol. 1988, 8, 2999–3007). It has also been found that residue 15 (phenylalanine) is an important receptor contact; Mol. Cell. Biol. 1988, 8, 2999–3007.

Unfortunately none of the synthetic peptides reported above have been shown to possess significant potential as EGF Receptor agents. Thus there currently exists a need for novel growth factor analogs (or other growth factor receptor ligands) for use in the investigation or manipulation of growth factor mediated processes and diseases.

The present invention has now provided novel growth factor analogs and methods of preparation of such analogs that address shortcomings of the prior art.

According to a first aspect of the present invention there is provided a peptide comprising an amino acid sequence corresponding to Sequence I.D. No 3 or a sequence wherein the amino acids of Sequence I.D. No 3 are replaced by conservative substitutions or a sequence having 90% homology to either of these peptide sequences characterised in that the amino acid at position 10 of Sequence I.D. No 3 or the sequences conservatively substituted or homologous thereto is a bicyclic proline analog and in that a disulphide bridge is provided between the cysteine residues at positions 1 and 12.

By bicyclic proline analog is meant any azabicycloalkane carboxylic acid or azabicycloalkene (monounsaturated) carboxylic acid or derivatives thereof.

A comparison of Sequence I.D. No 3 and Sequence I.D. No 2 shows that the peptides of the current invention broadly correspond to the central portion of authentic TGFA (which forms a part of the B-loop). However they differ in a number of important respects. It is these important differences which confer unexpected and industrially applicable properties on the peptides including, inter alia, growth factor receptor activity.

By 'growth factor receptor activity' is meant either the ability to induce mitogenic activity, or to interact with the EGF Receptor (or both).

By 'mitogenic activity' is meant the ability to induce increased DNA synthesis in cell lines, and in particular in fibroblasts for example human fibroblasts. Methods for assaying mitogenic activity are well known to those skilled in the art (see, for example, Davies, D. E. et al, Br. J. Cancer 1994, 70, 263–269).

By 'interact with the EGF Receptor' is meant the ability to act as either an agonist or antagonist (with respect to authentic TGFA) therefor.

Agonist activity may be deduced inter alia from studying the mitogenic response of a cell line responsive to EGF or TGFA to the novel peptides, or assaying second messengers associated with this response. It may also include tyrosine phosphorylation, for example EGF-R tyrosine phosphorylation, but it is not necessary for it to do so.

Antagonist activity may be deduced inter alia by binding studies with labelled TGFA, or by observations of the TGFA-induced response in presence of the peptides.

Significantly—it has not been possible to demonstrate growth factor receptor activity with the 'authentic' B-loop TGFA fragments of the prior art.

One way in which the peptides made available by the present invention differ from those in the prior art (both EGF and TGFA fragments) is that they contain a synthetic (ie non-naturally occurring) amino acid.

It is well known that there are twenty different types of naturally occurring amino acid commonly found in proteins and polypeptides. Each (apart from glycine) has an assymetric carbon atom bonded to a hydrogen atom, an amino group or imino group, a carboxyl group, and a distinctive side-chain, and each occurs naturally in the L-form. The peptide bond shows a high degree of resonance stabilisation such that they have a degree of double bond character and cannot rotate freely. These peptide bonds generally exist in the trans- form with respect to the assymetric carbons. However, proline is an exception to this wherein the pyrollidine structure and the N-alkylated amide bond lead to a smaller rotational barrier giving rise to cis- and trans-peptide bonds of comparable energy.

The bicyclic proline analogs incorporated into the peptides of the current invention differ from proline proper in that they have a bicyclic side-chain. Examples of possible analogs include 2-azabicyclo[2,2,1]heptane-3-carboxylic acid and 2-azabicyclo[2,2,2]octane-3-carboxylic acid, and substituted derivatives thereof.

Bicyclic and monocyclic proline analogs having unnatural ring sizes or substitutions at the 3,4 and 5 position have been prepared but few have been incorporated into peptides and none into EGF or TGFA analogs.

Preferably the bicyclic proline analog is 2-azabicyclo[2,2,1]heptane-3-carboxylic acid and more preferably it is in the D-form (1R, 3R, 4S form) (hereinafter referred to as 'DABHC').

However, any bicyclic proline analog wherein the rigidity of the side chain is enhanced with respect to proline proper, thereby limiting rotation about one or both of the peptide bonds which form adjacent to the analog may be suitable.

Analogs wherein the interactions between the side-chain and the peptide bond formed by the imino group are such as to lower the energy associated with the cis form of the peptide bond formed by the imino group are particularly suitable. By stabilising the cis form of the peptide bond, the peptide may be constrained into (or favour) a conformation which would not ordinarily be favoured by peptides containing proline proper or other amino acids.

These peptides further differ from the prior art peptides in that they are cyclised by means of a disulphide bridge between residues 1 and 12 of Sequence I.D. No 3. This bridge is not present in authentic TGFA, but has been included in these peptides for the purpose of enhancing their growth factor receptor activity.

The invention embraces peptides comprising an amino acid sequence corresponding to sequences wherein the amino acids of Sequence I.D. No 3 are replaced by conservative substitutions.

By 'conservative substitution' is meant the substitution of an amino acid by another one of the same class; the classes being as follows:

| Class | Examples of Amino Acid |
| --- | --- |
| Nonpolar | Ala, Val, Leu, Ile, Pro, Met, Phe, Trp |
| Uncharged polar | Gly, Ser, Thr, Cys, Tyr, Asn, Gln |
| Acidic | Asp, Glu |
| Basic | Lys, Arg, His |

The above table includes D and L amino acids.

Other substitutions may also be made according to the following table:

| Class | Examples of Amino Acid |
| --- | --- |
| Aromatic | Phe, Tyr, His |
| Proton Donor | Asn, Gln, Lys, Arg, His, Trp |
| Proton Acceptor | Glu, Asp, Thr, Ser, Tyr, Asn, Gln |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Indeed, such changes may confer slightly advantageous properties on the peptide. Suitable conservative substitutions within Sequence I.D. No 3 would include the substitution of arginine 2 for lysine, glutamine 6 for asparagine or alanine 11 for valine.

The invention embraces peptides comprising an amino acid sequence having 90% homology to Sequence I.D. No 3 (or a sequence wherein the amino acids of Sequence I.D. No 3 are replaced by conservative substitutions as discussed hereinbefore). As is well known to those skilled in the art, substitutions to regions of a peptide which are not critical in determining its conformation may not greatly affect its activity because they do not greatly alter the peptide's three dimensional structure. Hence, such peptides (provided that they still contain the bicyclic proline analog and cysteine bridge) are encompassed by the present invention.

The invention also comprises a peptide comprising any of the amino acid sequences described above ie wherein the N- or C-terminus has been extended. Extension of the peptides above may confer additional desirable properties on them, for instance stronger binding affinity for the EGF Receptor. Suitable extensions include sequences corresponding to (or mimicing) other structural features or motifs of EGF or TGFA proper, for instance the A or C loops, or N- or C-termini.

The invention further makes available a peptide comprising an amino acid sequence corresponding to Sequence I.D. No 4 or a sequence wherein the amino acids of Sequence I.D. No 4 are replaced by conservative substitutions or a sequence having 90% homology to either of these peptide sequences characterised in that the amino acid at position 1 of Sequence I.D. No 4 or the sequences conservatively substituted or homologous thereto is phenylalanine or tryptophan and at position 11 is a bicyclic proline analog and in that a disulphide bridge is provided between the cysteine residues at positions 2 and 13.

Thus these peptides further differ from those in the prior art in that they contain phenylalanine or tryptophan at position 1 (which corresponds to threonine 20 in authentic TGFA). Preferably the residue at position 1 is phenylalanine. The aromatic residue is incorporated into these peptides for the purpose of enhancing their growth factor receptor activity.

Alternatively, instead of phenylalanine or tryptophan then tyrosine may be substituted at position 1.

The invention further encompasses use of any of the above peptides wherein the growth factor receptor activity comprises mitogenic activity in promoting mitogenesis, and in particular in promoting cell replication. Such use may have application in research or in accelerated wound healing.

Similarly, the invention further encompasses use of any of the above peptides which have EGF Receptor-agonist activity as agonists for the EGF Receptor.

The invention further encompasses use of any of the above peptides which have EGF Receptor-antagonist activity as antagonists for the EGF Receptor. Such use may have application in research or in the treatment of EGF Receptor related disorders, or neoplastic or hyperproliferative diseases. Also embraced by the current invention are therapeutic compositions for these purposes which comprise the peptides above.

Thus the invention makes available peptides which have a wide application in the research or manipulation of growth factor mediated processes. Such peptides can be readily manufactured using processes based on those already used by those skilled in the art.

The peptides and processes of the present invention will now be described, by way of illustration only, through reference to the following examples. Other embodiments falling within the scope of the invention will occur to those skilled in the art in the light of these.

FIGURES

FIG. 1. shows the mitogenic activity of the peptide made in Example 1 (incorporating DABHC) (a) compared with corresponding peptides incorporating (b) LABHC, (c) D-proline or (d) L-proline.

Figure 2:
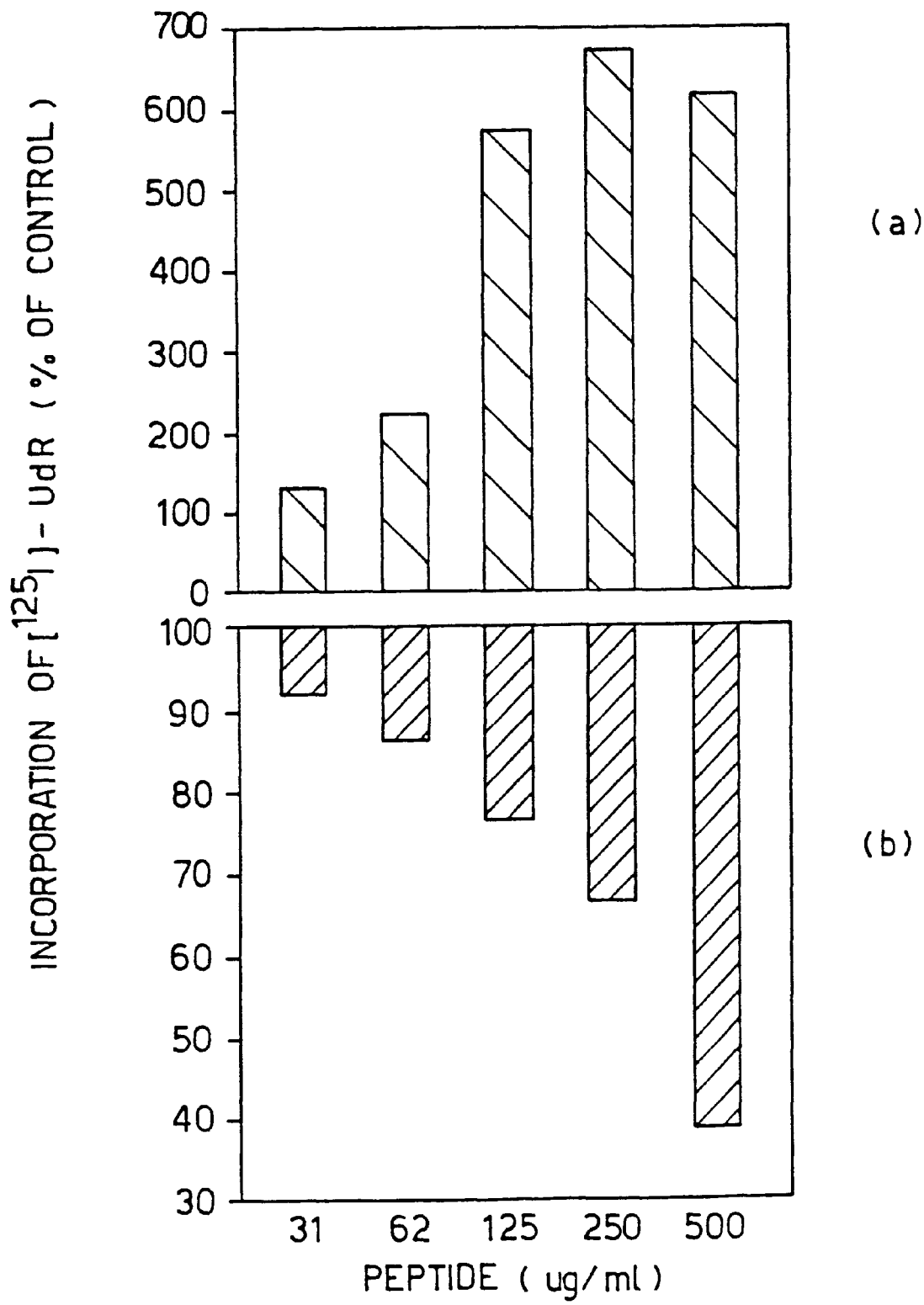

FIG. 2. shows the effect of the Example 1 peptide on the mitogenic response induced by sub-optimal concentrations of TGFA (a) and maximally stimulating concentrations of TGFA (b).

Figure 3:
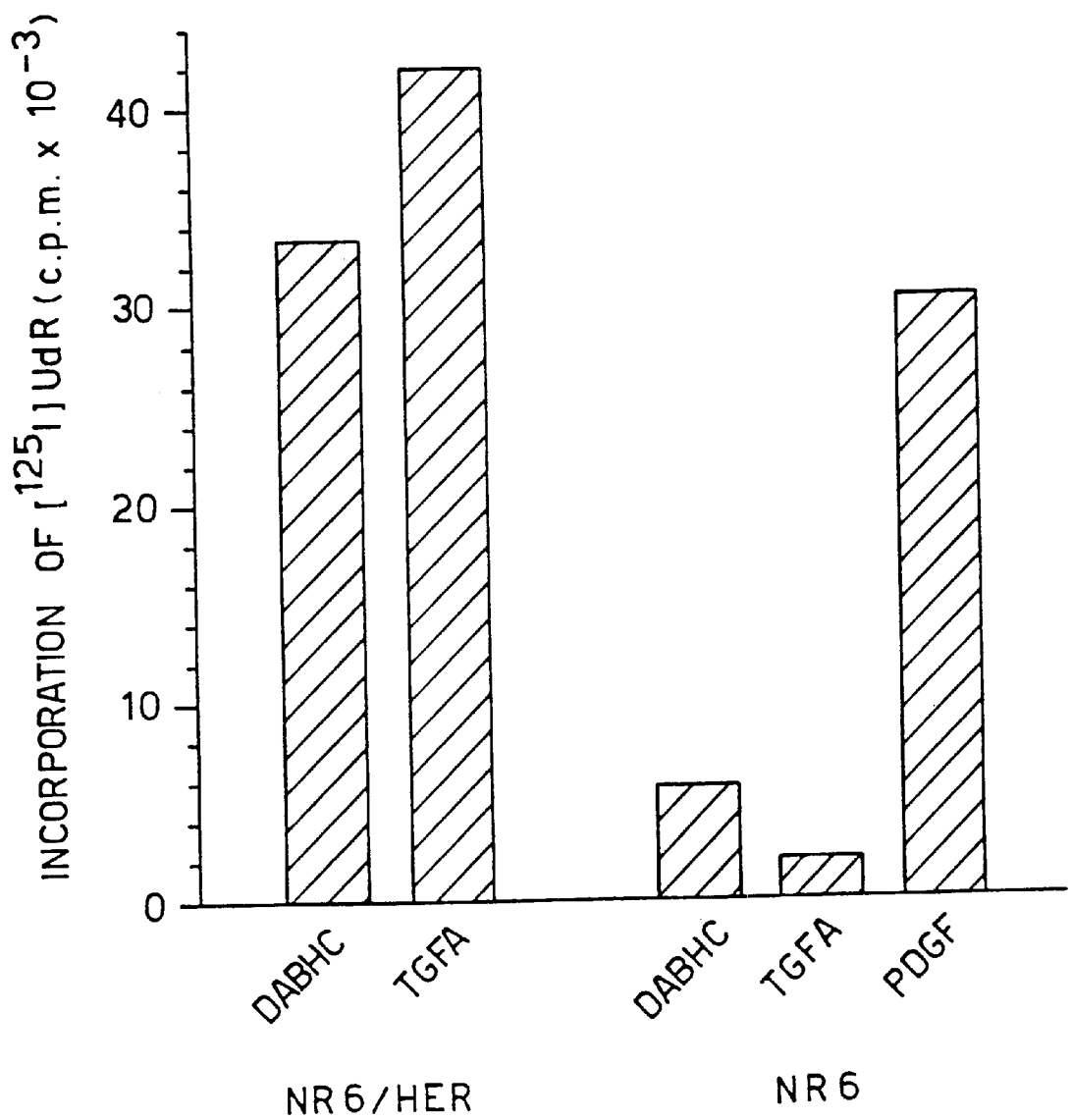

FIG. 3. compares the mitogenic activity of the example 1 peptide on NR6 fibroblasts (EGF-R⁻) and NR6/HER (EGF-R⁺) fibroblasts.

SEQUENCE LISTINGS

Sequence I.D. No 1 corresponds to human EGF.
Sequence I.D. No 2 corresponds to human TGFA.
Sequence I.D. No 3 corresponds to a first novel peptide of the present invention wherein the amino acid at position 10 is a bicyclic proline analog, and a disulphide bridge is provided between the cysteine residues at positions 1 and 12.
Sequence I.D. No 4 corresponds to a second novel peptide of the present invention wherein the amino acid at position 1 is phenylalanine or tryptophan and at position 11 is a bicyclic proline analog, and a disulphide bridge is provided between the cysteine residues at positions 2 and 13.

EXAMPLES

Example 1

Synthesis of Peptide in Accordance with Sequence I.D. No 4

A peptide according to Sequence I.D. No 4 wherein X1 was phenylalanine and X11 was DABHC was manufactured as follows:

DABHC SYNTHESIS

DABHC was synthesised in accordance with methods known in the art (see, for example, Gaitanopoulos, D. E. et al, J. Heterocycl. Chem. 1985, 22, 4, 957–959; patent DE 3246757 (Henning R., et al); patent FR 2525604 (Vincent M., et al); patent JP 78143278 (Sanraku-Ocean Co., Ltd).

PEPTIDE SYNTHESIS

The peptide was synthesised by linear assembly via solid phase methods using 9-fluorenylmethoxycarbonyl chemistry followed by construction of the disulphide bond linking the Cys residues. Assembly followed standard procedures using the following protecting groups, Cys (trityl), Arg (pentamethylchroman sulphonyl), Asp and Glu (t-butoxy) and Lys (t-butoxylcarbonyl). The peptide was cleaved from the 4-hydroxymethylphenoxymethyl resin with 95% trifluoroacetic acid (TFA). The linear peptide was converted to a cyclic peptide by air oxidation in ammonium bicarbonate solution at 38° C.

PEPTIDE PURITY

Final purification by HPLC was achieved by gradient elution on Reverse-Phase HPLC using TFA/$H_2O$ TFA/MeCN 5% to 95%. The peptide was homogenous by HPLC. Mass spectroscopy established the required molecular weight and amino acid analysis showed the presence of all residues apart from DABHC and Cys. The sequence was confirmed by 2-D NMR.

Example 2

Growth Factor Receptor Activity of Example 1 Peptide

The mitogenic and EGF Receptor activity of the Example 1 peptide was studied as follows:

MATERIALS

Materials came from the following sources: Recombinant hEGF (Life Technologies, UK); recombinant hTGFA (British Biotechnology); NR6/HER cells [NR6 fibroplasts transfected with hEGF Receptor] (Ludwig Institute for Cancer Research, UK).

CELL CULTURE

NR6 and NR6/HER cells (NR6 mouse fibroblasts transfected with human EGF-R expression plasmid) and HN5 squamous carcinoma cells (see Cowley, G. P. et al, Br. J. Cancer 1986, 53, 2230229) were routinely cultured in Dulbecco's Modified Eagles Medium (DMEM) containing 10% foetal bovine serum (FBS), 2 mM glutamine, non-essential amino acids, 10 U/ml penicillin and 10 μg/ml streptomycin at 37° C. in a humidified atmosphere of air containing 5% $CO_2$. G418 (100 μg/ml) was also included in the NR6/HER growth medium as selection for EGF Receptor encoding transformants.

MITOGENIC ACTIVITY

The ability of the Example 1 peptide to induce DNA synthesis in confluent and quiescent cells was assayed as described in Davies, D. E. et al, Br. J. Cancer 1994, 70, 263–269 but using NR6/HER or NR6 cells in place of human foreskin fibroplasts. The results are shown in FIGS. 1 and 2.

The Example 1 peptide (incorporating DABHC) stimulated DNA synthesis with an $EC_{50}$ value of 130 μM (FIG. 1(a)). Corresponding synthesis and testing of the equivalent peptide incorporating LABHC yielded a value of 330 μM (FIG. 1(b)). Corresponding peptides using D- or L-proline proper were inactive (FIGS. 1(c) and (d) respectively). All four peptides were inactive in linear, free sulphydryl form. These results clearly demonstrate the usefulness of the peptides provided by the present invention, as mitogenic agents and the importance of the bicyclic proline analog and the disulphide bridge.

The Example 1 peptide induced a similar maximal mitogenic response to a maximal dose of authentic TGFA. At suboptimal doses of TGFA, the Example 1 peptide produced an additive response up to the plateau level of stimulation by TGFA (FIG. 2(a)). However, at maximal doses of TGFA, the Example 1 peptide reduced the mitogenic response (FIG. 2(b)). Similar, but less pronounced, results were found for the corresponding peptide incorporating LABHC. Corresponding peptides using D- or L-proline proper did not yield the same effect. These results clearly indicate the usefulness of the peptides of the current invention as EGF Receptor agonist and antagonists.

In order to establish that the DABHC peptide interacted with EGF-R its activity was assessed on the parental NR6 cell line which lacks EGF-R (FIG. 3).

The NR6 cells showed a mitogenic response to doses of DABHC or TGFα which were maximally stimulating for NR6/HER cells. The responsiveness of the cells to a mitogenic stimulus was confirmed in the presence of PDGF.

EGF Receptor Tyr PHOSPHORYLATION

EGF Receptor Tyr phosphorylation assays were performed using HN5 cells at approximately 50% confluence in 96-well plates. Cells were plated in 10% FBS/DMEM and allowed to adhere overnight. Medium was removed and wells washed twice with DMEM. The peptide was diluted in DMEM and added in 50 μl volume and cells incubated for 10 minutes at room temperature. At the end of incubation, reagents were removed and the cells washed once with 50 μl/well buffered saline and then rapidly solubilised with 50

μl/well×1 sample buffer containing phosphatase and protease inhibitors (1 mM NaF, 1 mM Na$_3$VO$_4$, 100 μM PMSF). Enhanced phosphorylation of the 170 kDa EGF-R was determined by Western Blotting after SDS polyacrylamide gel electrophoresis as in Holt, S. J. et al, Biochem. Pharmacol. 1994, 47, 117–126.

Neither the Example 1 peptide nor the corresponding peptide incorporating LABHC appeared to lead to increased EGF Receptor phosphorylation. This demonstrates the possible basis for their antagonist activity. EGF-R tyrosine phosphorylation is not a pre-requisite for induction of DNA synthesis (Decker, 1993, J. Biol. Chem. 268, 9176–79).

---

We claim:

1. A peptide having growth factor receptor activity and comprising an amino acid sequence corresponding to Sequence I.D. No. 3 or a sequence wherein the amino acids of Sequence I.D. No. 3 are replaced by conservative substitutions or a sequence having 90% homology to either of these peptide sequences wherein the amino acid at position 10 of Sequence I.D. No. 3 or the sequences conservatively substituted or homologous thereto is a bicyclic proline analog and in that a disulphide bridge is provided between the cysteine residues at positions 1 and 12.

2. A peptide as claimed in claim 1 wherein the bicyclic proline analog is an azabicycloalkane carboxylic acid or derivative thereof.

3. A peptide as claimed in claim 2 wherein the azabicycloalkane carboxylic acid is 2-azabicyclo[2,2,1]heptane-3-carboxylic acid.

4. A peptide as claimed in claim 3 wherein the 2-azabicyclo[2,2,1]heptane-3-carboxylic acid is in the D-form.

5. A method of treating EGF receptor related disorders, or neoplastic or hyperproliferative disease, said method comprising administering to a patient in need thereof, a therapeutic amount of a peptide according to claim 1.

6. A peptide having growth factor receptor activity and comprising an amino acid sequence corresponding to Sequence I.D. No. 4 or a sequence wherein the amino acids of Sequence I.D. No. 4 are replaced by conservative substitutions or a sequence having 90% homology to either of these peptide sequences wherein the amino acid at position 1 of Sequence I.D. No. 4 or the sequences conservatively substituted or homologous thereto is a phenylalanine or tryptophan and at position 11 is a bicyclic proline analog and in that a disulphide bridge is provided between the cysteine residues at positions 2 and 13.

7. A peptide as claimed in claim 2 wherein the amino acid at position 1 is phenylalanine.

8. A peptide as claimed in claim 1 or claim 2 wherein the growth factor receptor activity comprises mitogenic activity.

9. A method for promoting mitogenesis in a cell, said method comprising applying to said cell an effective amount of a peptide according to claim 8.

10. A method for promoting wound healing in a mammal, which method comprises applying to said wound, an effective amount of a peptide according to claim 8.

11. A peptide as claimed in claim 1 or claim 2 wherein the growth factor receptor activity comprises agonist activity.

12. A peptide as claimed in claim 1 or claim 2 wherein the growth factor receptor activity comprises antagonist activity.

13. A method of treating EGF receptor related disorders, or neoplastic or hyperpoliferative disease, said method comprising administering to a patient in need thereof, a therapeutic amount of a peptide according to claim 2.

14. A therapeutic composition for the treatment of EGF Receptor related disorders neoplastic or hyperproliferative diseases which comprises together with a pharmaceutically-acceptable carrier or diluent a peptide as claimed in claim 1 or 2.

15. A peptide comprising an amino acid sequence corresponding to Sequence I.D. No. 3 or a sequence wherein the amino acids of Sequence I.D. No. 3 are replaced by conservative substitutions wherein the amino acid at position 10 of Sequence I.D. No. 3 or the sequences conservatively substituted is a bicyclic proline analog and in that a disulphide bridge is provided between the cysteine residues at positions 1 and 12.

16. A peptide comprising an amino acid sequence corresponding to Sequence I.D. No. 4 or a sequence wherein the amino acids of Sequence I.D. No. 4 are replaced by conservative substitutions wherein the amino acid at position 1 of Sequence I.D. No. 4 or the sequences conservatively substituted or homologous thereto is a phenylalanine or tryptophan and at position 11 is a bicyclic proline analog and in that a disulphide bridge is provided between the cysteine residues at positions 2 and 13.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 53 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Homo sapiens (ix) FEATURE:
       (A) NAME/KEY: Disulfide-bond
       (B) LOCATION: 6..20

(ix) FEATURE:
       (A) NAME/KEY: Disulfide-bond
       (B) LOCATION: 14..31

(ix) FEATURE:
       (A) NAME/KEY: Disulfide-bond
       (B) LOCATION: 33..42

(xi) SEQUENCE DESCRIPTION: SEQ ID NO:1:

```
Asn Ser Asp Ser Glu Cys Pro Leu Ser His Asp Gly Tyr Cys Leu His
1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asn Leu Lys
        35                  40                  45

Trp Trp Glu Leu Arg
    50
```

(2) INFORMATION FOR SEQ ID NO:2:

(i) SEQUENCE CHARACTERISTICS:
       (A) LENGTH: 50 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Homo sapiens (ix) FEATURE:
       (A) NAME/KEY: Disulfide-bond
       (B) LOCATION: 8..21

(ix) FEATURE:
       (A) NAME/KEY: Disulfide-bond
       (B) LOCATION: 16..32

(ix) FEATURE:
       (A) NAME/KEY: Disulfide-bond
       (B) LOCATION: 34..43

-continued (xi) SEQUENCE DESCRIPTION: SEQ ID NO:2:

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Disulfide-bond
        (B) LOCATION: 1..12

(xi) SEQUENCE DESCRIPTION: SEQ ID NO:3:

Cys Arg Phe Leu Val Gln Glu Asp Lys Xaa Ala Cys
1               5                   10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Disulfide-bond
        (B) LOCATION: 2..13

(xi) SEQUENCE DESCRIPTION: SEQ ID NO:4:

Xaa Cys Arg Phe Leu Val Gln Glu Asp Lys Xaa Ala Cys
1               5                   10